United States Patent [19]
Lappe

[11] Patent Number: 6,036,092
[45] Date of Patent: *Mar. 14, 2000

[54] ON-SITE MACHINE READABLE ASSAYING ARRANGEMENT

[76] Inventor: Murray Lappe, 9570 Heather Rd., Beverly Hills, Calif. 90210

[*] Notice: This patent is subject to a terminal disclaimer.

[21] Appl. No.: 09/018,487

[22] Filed: Feb. 4, 1998

Related U.S. Application Data

[63] Continuation of application No. 08/832,957, Apr. 4, 1997, Pat. No. 5,929,422.

[51] Int. Cl.$^7$ .............................. G01N 33/48; G06F 7/10
[52] U.S. Cl. .............. 235/462.13; 235/375; 235/462.04; 422/56
[58] Field of Search ...................... 235/462.01, 462.13, 235/462.04, 375, 499; 422/56, 66

[56] References Cited

U.S. PATENT DOCUMENTS

| | | | |
|---|---|---|---|
| 4,042,329 | 8/1977 | Hochstrasser | 436/71 |
| 4,059,407 | 11/1977 | Hochstrasser | 436/71 X |
| 5,902,982 | 5/1999 | Lappe | 235/375 |
| 5,929,422 | 7/1999 | Lappe | 235/462.13 |

*Primary Examiner*—Michael G Lee
*Assistant Examiner*—Drew A. Dunn
*Attorney, Agent, or Firm*—Goldstein & Conino

[57] ABSTRACT

A machine readable assaying system including a test card providing a machine readable assaying arrangement. At least one analysis strip is provided, possibly including antibodies and or reagents capable of detecting and optically indicating the presence or absence of at least one substance present within a volume of physiological fluid. The analysis strips composing, at least in part, an assaying mechanism in the form a pattern of elements, generally additionally including at least one fixed strip, and at least one blank region. Each analysis strip, upon contacting the physiological fluid of a donor for a suitable temporal interval, may effect a change from a first state having a first reflectance level to a second state having a second substantially different reflectance level, thereby altering the pattern formed by the assaying mechanism. The particular pattern that results from an exposure to the volume of the physiological fluid is contemplated to produce a distinct machine readable indicia. The assaying system may also include a scanner and decoder to optically scan and read the machine readable indicia and transmit read information over a communication link to a remote location for processing. In a most preferred embodiment of the system, the transformation of the pattern, which occurs on the test card, will not be readable or interpretable by the administrator of the test/assay, thus preserving the anonymity and privacy of the tested individual.

10 Claims, 6 Drawing Sheets

ON-SITE MACHINE READABLE ASSAYING ARRANGEMENT

CROSS REFERENCE TO RELATED APPLICATIONS

The subject matter of this application represents a continuation of application Ser. No. 08/832,957 filed on Apr. 4, 1997 now U.S. Pat. No. 5,929,422.

BACKGROUND OF THE INVENTION

1. Field of the Invention

The invention relates to assaying systems. More particularly, the invention relates to embodiments of machine readable assaying systems for analyzing a volume or specimen of physiological fluid to detect the presence, or absence, of particular substances therein.

2. Background and Objects of the Invention

The need to maintain confidentiality when performing an assay for substances that may be present in a volume of physiological fluid excreted or drawn from a donor is known in the art. If this confidentiality requirement extends to the assay administrator, the problem is exasperated, especially if the assay is to be performed 'on-site', say, at a place of employment. The confidentiality concerns remain valid whether attempting to detect the presence of a virus, the residue of a proscribed (e.g., illegal) drug, or other substances/items.

For example, the increase in the use of recreational drugs over the past several decades has created a sharp need for more effective, expeditious methods of analyzing whether a donor has used one or more proscribed substances. The need applies to a wide range of situations ranging from the testing of prospective employees for drug abuse, to the testing of race horses or athletes for the use of stimulants and enhancers. Consider the needs of private industry employers, as well as governmental agencies, to determine whether an individual has drug residue present in his or her (biological) system. Typically, the status of an individual as a substance abuser is determined by analysis of the individual's physiological fluids, namely urine. A volume of urine is collected, and a highly sensitive screening test performed, usually at a remote and centralized facility. If the volume tests positive at the central facility, then a second, possibly more sensitive, controlled confirmation analysis is generally performed.

The above procedure is plagued by several inherent and undesirable characteristics. In addition to potentially being a costly process, the above mentioned procedure also involves great time delays to employers desirous of obtaining new qualified employees. Upon collection of the urine sample, the employer must wait to receive test results from the central facility before hiring potential employees. Furthermore, the occurrence of errors due to the significant amount of handling, and the transfer of the volume from the initial collection site to the central facility, is problematic. Although, the confidentiality of donors is addressed through the use of the central (remote) facility, new and improved assaying systems and arrangements are needed.

To combat the above mentioned problems, which are faced by many private and corporate entities, various "on-site" or "hand-held" assaying devices have been developed. One major problem inherent in these "on-site" testing devices is that the privacy concerns of the potential employee being tested are not adequately addressed. Since generally all of the on-site testing devices available heretofore attempt merely to identify substances present (i.e. simply to indicate which specimens do indeed possess the substance being checked for), the anonymity of a presumptive positive donor is generally impossible to conceal. Due to such a lack of anonymity, many employers (governmental in particular) will not employ such assaying systems or devices as they do not comply with federally mandated regulations regarding the privacy and civil liberties of donor individuals.

Objects of the present invention are, therefore, to provide new and improved on-site assaying system having one or more of the following capabilities, features, advantages and/or characteristics:

- an assaying system for analyzing a volume of physiological fluid to detect the absence or presence of at least one proscribed substance contained therein;
- a reliable and expeditious on-site assaying system wherein "results" are transmitted to and or stored at a remote location, such as a central facility for review (processing) and interpretation;
- maintains the privacy and anonymity of a donor (e.g., a prospective employee);
- provides test means wherein changes and results detected are not "human readable", and thus are not subject to interpretation and possibly unauthorized dissemination.
- a method of operation wherein test results can be obtained quickly without compromising the privacy concerns of the donor individuals being tested and or screened;
- an on-site, portable assaying system;
- an assaying system which allows the results of said assay to be encoded in a machine readable format (such as bar-coded indicia) such that the encoded results are visually undetectable and must be de-coded by appropriate apparatus;
- assaying means includes analysis strips that upon contacting, in a suitable manner, the physiological fluid to be tested, are capable of providing an optically detectable machine readable change indicating the presence or absence of one or more substances (within the fluid);
- inherently configurable to restrict an assay administrator's access to the assay results;
- a remote location may be efficiently employed to indicate the outcome of the assay activities, rapidly via "electronically" exchanged information and data, for example by way of a communication link established by a network or modem.
- may employ conventional bar-code reading apparatus, such as optical scanning units, to determine the (encoded) results of an assay;
- includes means capable of detecting adulteration of the volume of physiological fluid;
- includes means to determine if the assaying means is operating properly.

The above listed advantages, characteristics, objects, and or associated novel features of the present invention, as well as others, will become more clear from the description and figures provided herein. Attention is called to the fact, however, that the drawings are illustrative only. Variations are contemplated as being part of the invention, limited only by the scope of the appended claims.

SUMMARY OF THE INVENTION

In a preferred embodiment, the machine readable assaying system contemplates the utilization of machine readable bar-code like patterns located upon a test card which effects detectable changes in response to a physical, chemical or biological reaction, induced by contacting a portion of a volume of physiological fluid, such as urine, saliva, sweat, or blood specimens. The test result which is encoded within the bar-code indicia located upon the test card is read by an appropriate test card reading apparatus (e.g., a suitable bar-code reader/scanner), with the decoded source of data possibly stored in a memory unit and or transmitted, if desired, to a remote location for analysis and review. A test administrator merely scans the patterns present on the test card after a sufficient temporal period has elapsed (after the test card has properly contacted the physiological fluid). The detection of substances, possibly including proscribed or illicit substances (or residues thereof), and general assaying activities, are provided by analysis strips, in accordance with the present invention. Assaying means, incorporating the analysis strips, provide a machine readable source of data alterable to indicate the presence or absence of one or more substances, which may be arranged so that the optical change (and associated test result) is un-decipherable by a test administrator or another observer—while being readily machine readable. Accordingly, the privacy interests of the donor or donor individuals are preserved, while errors due to human interpretation, transcription, and translation, are reduced or eliminated.

BRIEF DESCRIPTION OF THE DRAWINGS

In the drawings, like elements are assigned like reference numerals. The drawings are not necessarily to scale, with the emphasis instead placed upon the principles of the present invention. Additionally, each of the embodiments depicted are but one of many possible arrangements utilizing the fundamental concepts of the present invention. As such, the embodiments illustrated should be considered illustrative only. The drawings are briefly described as follows.

LIST OF REFERENCE NUMERALS USED IN THE DRAWINGS

10—assaying system (example embodiment)
12—exemplary functional organization of remote location
22—test card
32—machine readable assaying means
33a—fixed strip (or bar)
33b—blank region (or space)
34—analysis strip (bar, space)
36—adulteration detection means
38—quality control indication means
42—identification code (pattern)
46—alignment aid
54—test card reader
54a—scanner
54b—decoder
55—bar code reader
56—control and communication means
58—central facility
60—test card reading apparatus
62—controller module
62a—processor
62b—memory unit
62c—interface circuitry
63—communication module
64—user interface module
64a—display
64b—keyboard
64c—audio unit
64d—printer
66—communication link
72—interpreter
76—encoder
82—test summary (receipt)
86—remote communication system
90—computer
92—hardcopy (print out)

DETAILED DESCRIPTION OF THE PREFERRED EMBODIMENTS

Figure 1A:
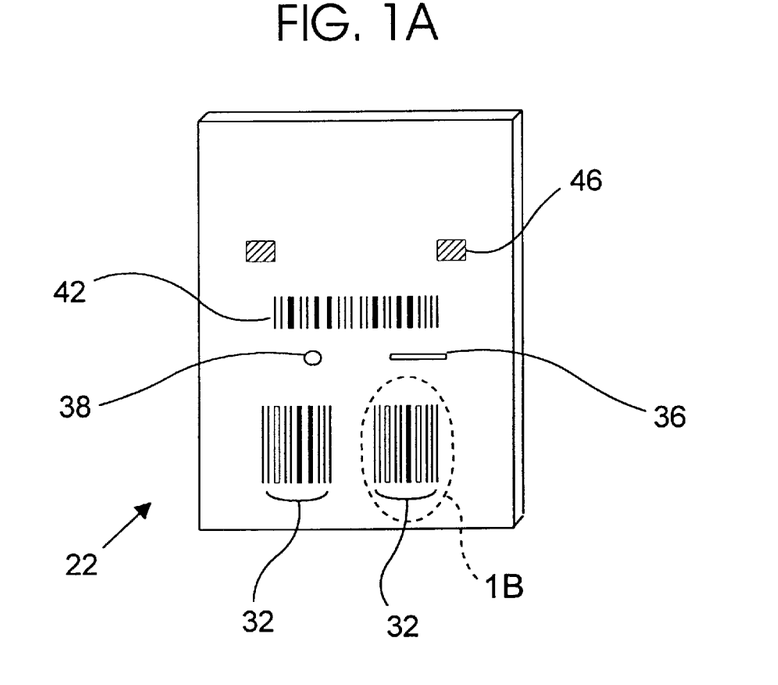
FIG. 1A illustrates a diagrammatic perspective view of a test card of an on-site machine readable assaying system.
Figure 1B:
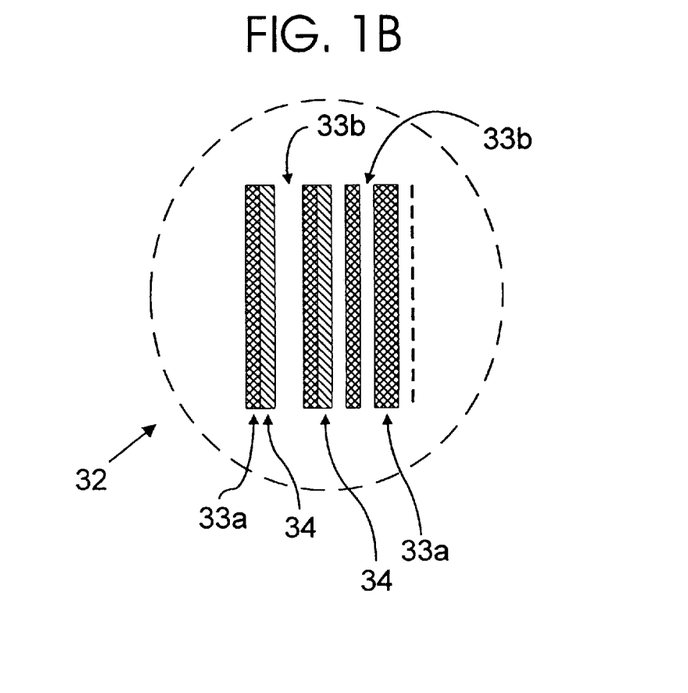
FIG. 1B illustrates an enlarged portion of the embodiment of the test card of FIG. 1A, in accordance with the invention.

FIG. 1 illustrates a test card 22 of an on-site machine readable assaying system (clearly depicted in FIG. 6), and generally designated as 10). As can be seen in FIG. 1, the test card 22, which may also be termed a substrate or as being comprised of a substrate, has located thereupon various indicia. More specifically, the test card 22 may be configured to include machine readable assaying means 32. Note: the term, "machine readable assaying means 32", may also be considered equivalent to "encoded machine readable source of data", "source of data including assaying strips", and very generally as a "source of data". Further, the terms "pattern" and "data pattern", are also to be assumed to be equivalent, as will be indicated in the following discussions. The machine readable assaying means 32 preferably comprise, at least in part, a plurality of individual analysis strips 34, which are best seen in FIG. 1B. In a preferred embodiment of the present invention the assaying means, including the analysis strips 34, may include antibodies and or reagents capable of chemically analyzing a sample volume of physiological fluid, such as human or animal urine, to detect and indicate the presence or absence of a particular substance. It is contemplated that such substances may be present as a result of the recent use of drugs (possibly including illegal drugs such as marijuana, cocaine, or heroin), or other substances such as bacteria and viruses. The assaying arrangement of the present invention may indeed be assumed to cover any parameter that may be determined via a physiological fluid of a donor.

It is important to understand that the detection and indication function of the assaying means 32 is induced by the contacting of the analysis strips 34 with the physiological fluid, for a sufficient temporal period. In a most preferred embodiment of the analysis strips 34, after the temporal period has elapsed, a change may have been effected in that the analysis strip 34 will have changed from a first state having a first reflectance level to a second state having a second substantially different (i.e. machine detectable) reflectance level. Therefore, this substantially different reflectance level change may result in an optically detectable "change", which in accordance with the present invention, may be employable to alter, for example a pattern formed by a plurality of elements, including at least one fixed strip 33a, at least one blank region 33b, and one or more analysis strips 34. This pattern (of elements) may be configured as, and referred to, as a series of bars and spaces (especially as applied to bar code indicia) and represents an example of a machine readable source of data. The machine readable source of data (e.g., the pattern) may or may not result in the optical reflectivity change discussed above, and may accordingly indicate one of the presence of at least one specific substance (to be screened), or the absence of at least one specific substance. Indeed, if a plurality of analysis strips 34 are employed, each may be configured to detect and indicate distinct substances, by either providing the reflectivity change with the presence or absence of the substance. Further, it is contemplated that respective test cards 22 may be specifically configured with analysis strips 34 that may react differently to the same or similar substances.

Traditionally, assaying means have been configured merely to visually indicate the positive presence of particular substances. If a "positive" indication was given, it was automatically inferred that the donor individual who provided volume of physiological fluid (for example urine) tested positive. If the test was a drug abuse screening test, the individual or donor, may be assumed to be a drug user/abuser (although secondary testing is generally conducted to confirm these results). Accordingly, this type of assaying system, wherein positive results are clearly apparent to a test administrator, posed great threats to individual privacy and civil liberty concerns, and hence is generally considered unsatisfactory. The employment of the assaying means by the present invention, however, addresses this, as well as other deficiencies.

As seen in detail in FIG. 1B, the plurality of individual analysis strips 34 are illustrated as an essential component of an exemplary machine readable assaying means 32, such as a bar code indicia. As mentioned earlier, each of the analysis strips 34 may include antibodies and or reagents which are capable of optically indicating the positive presence or absence of distinct illicit substances. In particular, the machine readable assaying means 32 may be formed, as shown in FIG. 1B, of a pattern of elements including one or more fixed strips 33a, one or more blank regions 33b, and the analysis strips 34, to produce the encoded machine readable data source. In a preferred embodiment, the detection of the presence (or absence) of a particular substance or drug, may result in one or more of the analysis strips 34 changing from a first state, say optically reflective in nature, to a second state, say optically absorbent (or non-reflective) in nature—or visa versa. Of course, it is further contemplated that the change from the first state to a second state may not be visually detectable by the human eye. For example, optical changes that occur in the ultra-violet range, may be employed and scanned for by a suitable test card reading apparatus.

As seen in the arrangement depicted in FIG. 1B, the pattern of analysis strips 34, fixed strips 33a, and blank regions 33b (which may also be termed "bars" and "spaces" by those skilled in the art), when configured to compose the encoded machine readable data source may be provided to encode one or more characters/digits of information or data. Accordingly, by the inclusion of the analysis strips 34 along with the plurality of fixed strips 33a and blank regions 33b, the detection of one or more substances may cause the overall pattern of fixed strips 33a (bar), analysis strips 34 (bar, spaces), and blank regions 33a (spaces), to vary and hence result in the encoded information represented thereby being altered. For example, machine readable assaying means 32 comprising the encoded machine readable data source may be comprised of one or more bar code indicia whose pattern of bars and spaces (and associated coded digits) alter in accordance to the particular substances detected via the inclusion and location of respective analysis strips 34 within the bar code indicia.

It should be noted that it is contemplated in a preferred embodiment of the test card 22 that one or more of the individual analysis strips 34 which compose the bar code indicia of the machine readable assaying means 32 contain reagents or antibodies whose visual appearance is altered in response to the contacting of the physiological fluid, regardless of whether any particular substance is present within the fluid. Accordingly, a negative assay may be determined by one or more analysis strips 34 becoming darker (a space becoming a 'bar'), by one or more analysis strips 34 becoming lighter (a bar becoming a 'space'), or by no change. This characteristic may be helpful when employed to prevent an administrator of the test from learning the outcome of the assay. Therefore, only a suitable configured device, employed to decode the encoded bar code indicia, will be able to determine the results of the assay.

The test card 22 of FIG. 1A also includes adulteration detection means 36. The adulteration detection means 36 is configured to be capable of determining whether a particular specimen of fluid, such as urine or other physiological fluids known to skilled individuals, may have been tampered with by administering various checks including chemical analysis (to ensure that the chemical composition of said specimen is consistent with that of standard, non-adulterated physiological fluid), temperature analysis (to ensure, for example, that the specimen has been recently excreted from the donor and has not been brought to the test site by the donor from an earlier excretion), and or other known adulteration checks. Furthermore, quality control indication means 38 are also be present upon the test cards 22 to ensure that the analysis strips 34 are functioning properly. Said quality control indication means 38 may be configured to generate a signal upon contact with a portion of the volume of the physiological fluid, regardless of the presence or absence of one or more substances to be screened or checked for, to indicate that the analysis strips 34 have not been degraded due to, for example, improper storage, the test cards exceeding their shelf life, and the like. If the quality control indication means 38 fail to generate a signal upon contact with the volume of physiological fluid, the test card 22 may be assumed to be defective and should be discarded.

As those skilled in the art will recognize, it is often desirable to have items such as production batch numbers of the test card, a date of manufacture, the specific substances the test card is configured to detect, etc. As can be seen in FIG. 1A, the test card 22 may include an identification code 42, which may be provided as a machine readable pattern, for example a bar code indicia, which encodes the required "ID" information. As the identification information, for the most part, will generally be fixed at the time of manufacture, it is contemplated that such information may be provided as both human readable and machine readable, if advantageous or desirable. Also seen in FIG. 1A are alignment aids 46 that may be provided to aid in the alignment of the test card 22 for reading or scanning by a properly arranged device. It is important to note that other arrangements of the identification code 42, the quality control indication means 38, the adulteration means 36, and the assaying means 32 are possible and contemplated. For example, skilled persons will appreciate modifications such as including the quality control indication means 38 and the adulteration means 36 within the elements composing the assaying means 32. Accordingly, quality control indication means 38 and the adulteration means 36 may assist in determining the overall "coding" provided by said assaying means 32. In one embodiment of the present invention, it is contemplated that the quality control indication means 38 be provided with "control test strips" (not specifically illustrated), that are situated within the pattern of elements composing the assaying means 32, and are arranged to change state regardless of the composition of the specific physiological fluid being tested or checked, if advantageous. Still other modifications are possible and contemplated.

Figure 2A:
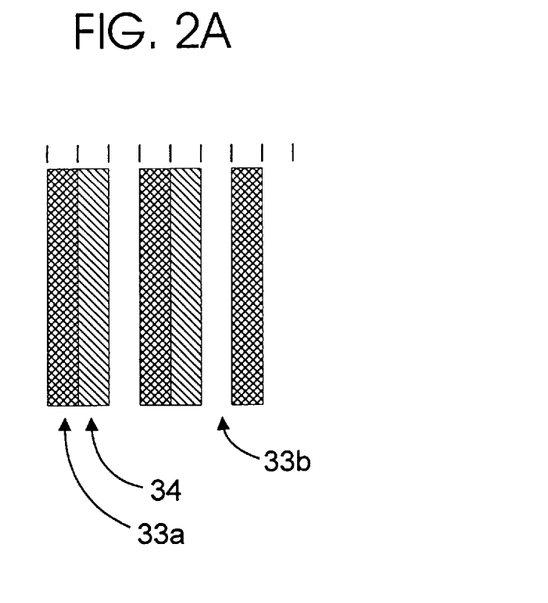
FIGS. 2A and 2B depict an embodiment of a coding arrangement providing exemplary character definitions.
Figure 2B:
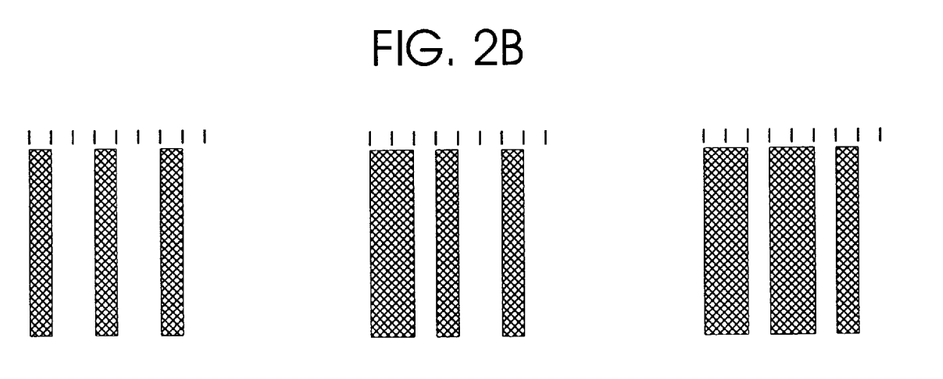

Referring now to FIG. 2A, there is depicted a sample arrangement of fixed strips 33a, blank regions 33b, and analysis strips 34. The analysis strips 34 may be assumed (for this example) to be of such a configuration, that upon contacting the physiological fluid, may change from a first state with a high level of (relative) reflectivity to a second state with a low level of reflectivity, if a change does indeed occur. As can be seen in FIG. 2B, with two analysis strips 34, a number of possible patterns may be generated or produced resulting in a variety of machine readable and decodable data patterns. Those skilled in the art will appreciate several considerations that must be addressed when employing standard and or known "symbologies", as well as the symbology exemplified in FIGS. 2A and 2B. First, many commonly employed bar-code symbologies include 'check digits' (and the like), as well as items such as guard bars, and start and stop characters. For example, the well known Code-39 symbology, includes a start character on the left side of a bar code and a stop character on the right side. In addition, check or error detecting characters must be considered when one or more analysis strips 34 change from a first state to a second state—especially if it is desirable to employ standard bar-code reading equipment with one or more embodiments of the present invention. Skilled individuals will appreciate these and other considerations that must be addressed to provide for the machine reading of the machine readable sources of data, including the assaying means and other items located upon the test card 22, of the present invention.

Figure 5:
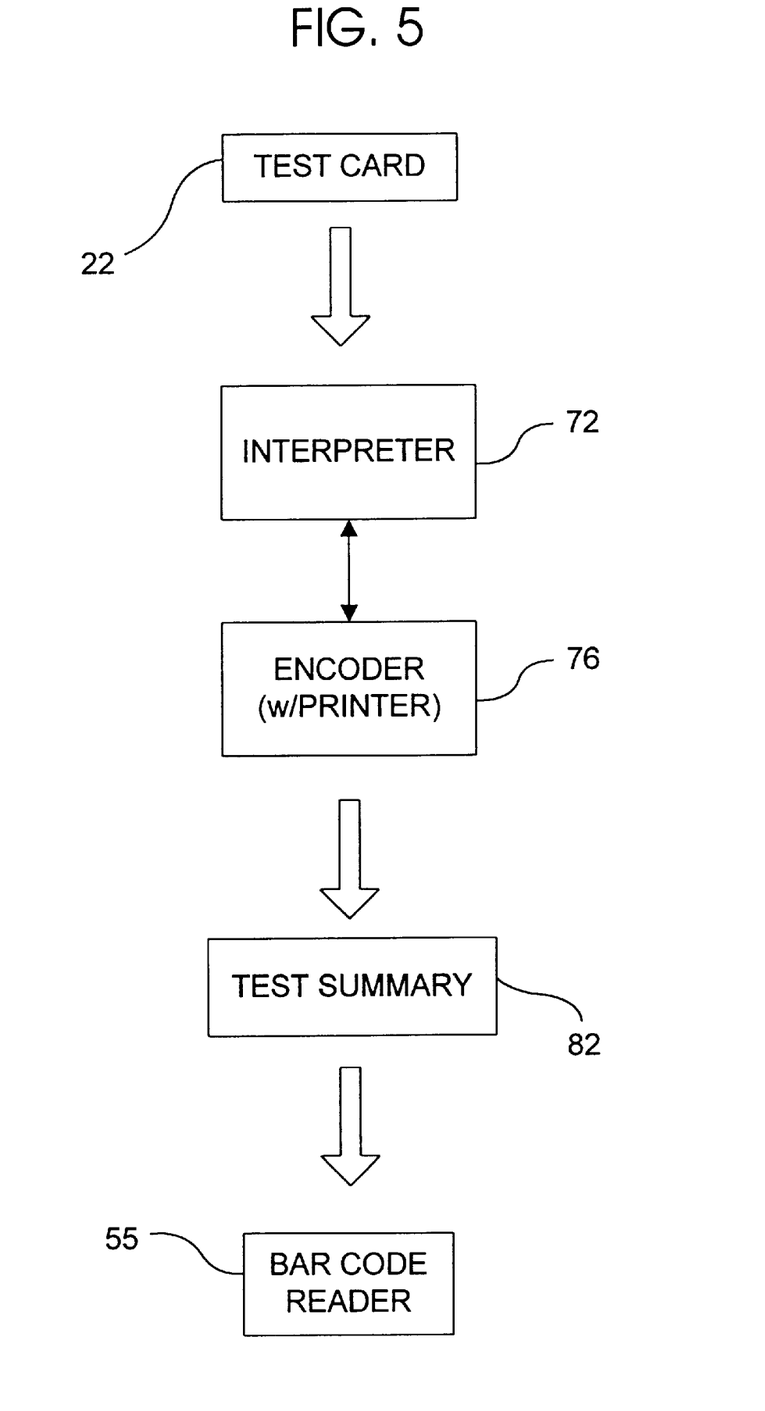
FIG. 5 provides another embodiment of an apparatus to read/interpret test cards of the present invention.

It should further be understood that the appearance of the bar-code like indicia, including identification code 42 or assaying means 32, as best seen in FIGS. 1A and 1B, may be provided in many contemplated optical forms. These forms include other patterns that may be devised and presented, which are optically very different in appearance to those illustrated (i.e., a standard bar-code type indicia). A key feature, especially considering the arrangement of FIG. 5, is the machine readability of the source of encoded data provided by any employed pattern.

Figure 3:
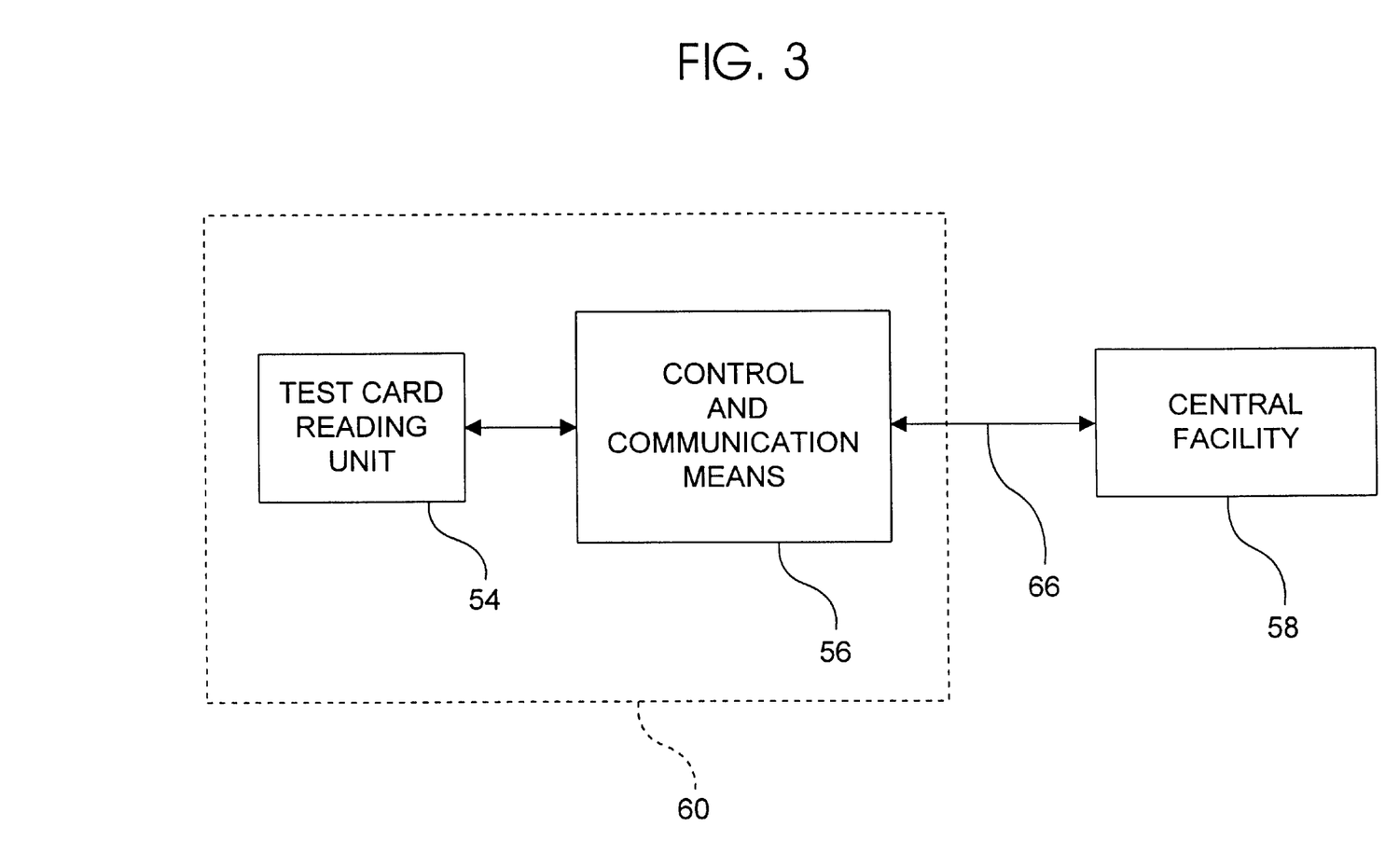
FIG. 3 is a high level functional diagram of an embodiment of an assaying apparatus to read/interpret a test card, such as that of FIG. 1A.

Turning now to FIG. 3, there is provided a high level functional block diagram of a test card reading apparatus 60. As shown, a test card reading unit 54 is included, which is operatively coupled to control and communication means 56. The test card reading means 54 is provided to "read" and determine the particular patterns present on the test card 22. As such, the reading of the patterns of the test card 22 may result in a plurality of digits or characters being determined (read), and possibly stored, by the test card reading unit 54, which may then be communicated to the control and communication means 56. Subsequently, the determined characters or digits may be transmitted, via a communication link 66, to a remote location, such as a central facility 58 for checking, decoding, and or general evaluation. Therefore, the pattern of the assaying means 32, the condition of the adulteration detection means 36 and the quality control indication means 38, and the identification code 42 information may be provided as "machine readable" and may be transmitted in an anonymous and confidential manner to the central facility 58, in accordance with the privacy features of present invention. Those skilled in the art will appreciate the available means to embody the test card 22 of FIG. 1A, and further may provide modifications and alterations to the embodiments of the test card reading apparatus 60 of FIGS. 3 and 4.

Figure 4:
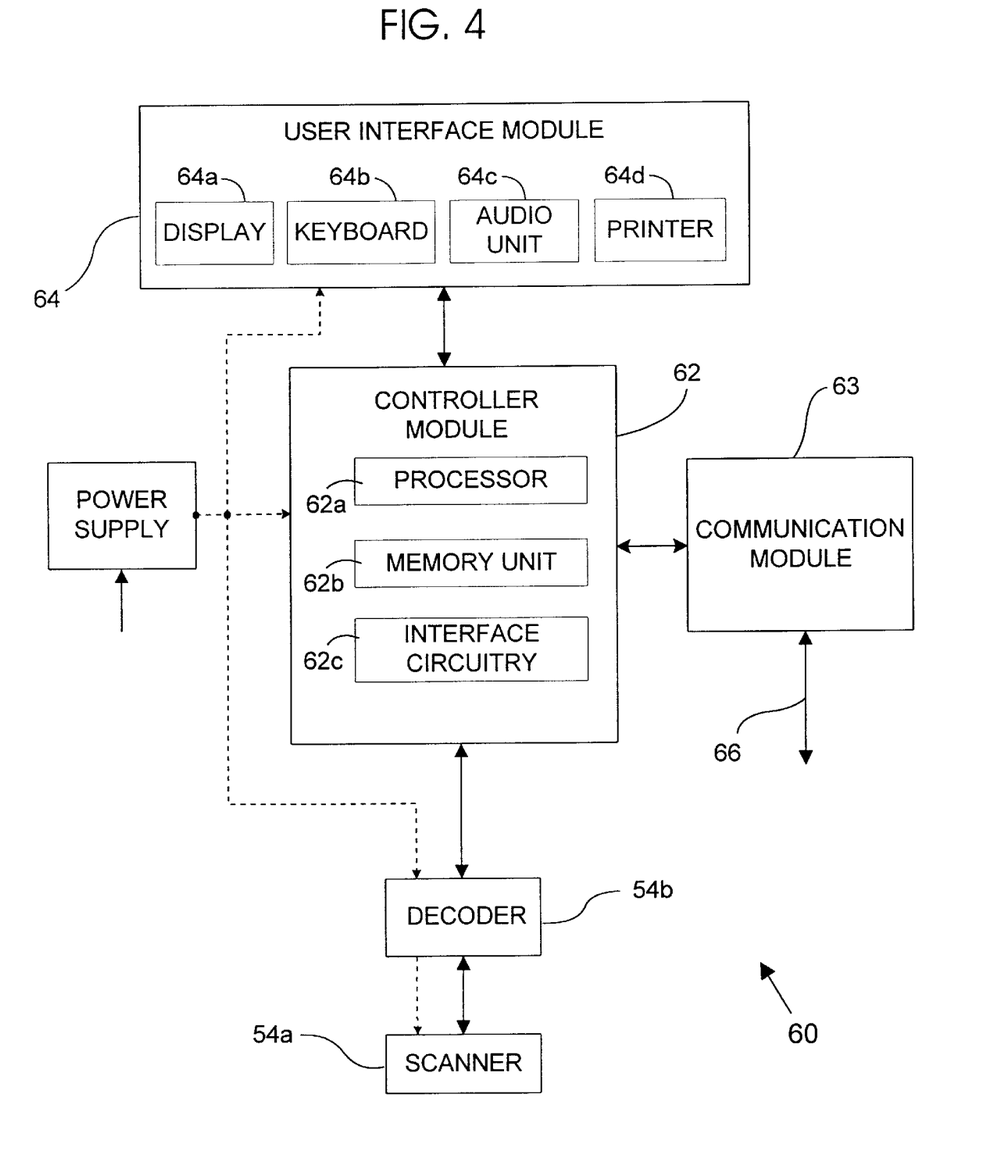
FIG. 4 provides a more detailed block diagram of an embodiment of the apparatus of FIG. 3.

One possible embodiment of the test card reading apparatus 60 is seen in FIG. 4. Included is a scanner 54a and decoder 54b configured to read the test card 22 and decode the plurality of patterns contained thereon. The patterns are encoding information carrying data, when either considered individually or in combinations. The patterns may provide the assaying means 32, the identification code 42, the adulteration detection means 36, the quality control indication means 38, and other like items. A controller module 62 is provided to establish the functional characteristics of the test card reading apparatus 60, as would be well understood by skilled persons. The controller module 62 may be embodied as shown by providing a processor 62a, a memory unit 62b (providing a suitable application program), and any required interface circuitry 62c. The controller module may be arranged to receive from the decoder information including one or more (decoded) digits or characters. The information may then be transmitted by a communication module 63 via the communication link 66 to the remote location (e.g., the central facility 58). The information processed and or transmitted to the central facility 58 for checking and analysis, and wherein a response may be provided back to the test card reading apparatus 60, possibly quite rapidly in a relatively short period of time, especially if a negative assaying result is determined.

Also shown in FIG. 4 is a user interface module 64 to enable an individual (such as an assay administrator) to enter information into the test card reading apparatus 60 and provide information to said individual. The user interface may include known items such as a display 64a, a keyboard 64b, an audio unit 64c, and printer 64d. For example, a case code identifying the donor, such as a social security number in the case of a human donor, may be entered into the system, say via keyboard 64B of the user interface module 64 and transmitted through the communication link 66 to the central facility 58. Other user interface items may also be provided (which are not shown in FIG. 4) including pointing devices, a fax transmission module, touch screen displays, etc. Such devices are known to skilled artisans.

It should be noted that the controller module 62 may be provided by known programmable single chip microcomputers and any additional analog/digital circuitry required. Further, it is contemplated that the controller module 62 may be provided (in an alternate embodiment to that shown in FIG. 4) by one or more programmable logic devices (PLDs), or by discrete components including digital MSI and LSI logic functions. Those skilled in the art will appreciate the plethora of commercially available (off-the-shelf) devices and components that may be utilized to embody the controller module 62 and the communication module 63. Also, although the scanner 54a may in a preferred embodiment be realized by an optical laser scanning device, other suitable devices, such as a CCD imaging device may be employed. It is also contemplated that the test card reading apparatus 60 may be realized by a properly configured personal or workstation computer. For example, an IBM® compatible personal computer (PC) may be arranged with a scanner 54a, a fax modem or networking card, etc., and a suitable custom application program. In such an embodiment, the functionality of the test card reading apparatus 60 may be provided by the execution of the application program. Therefore, it should be understood that the embodiments of the FIGS. 3 and 4 are illustrative of a number of possible functionally equivalent embodiments, which may be provided for the present invention.

An alternate embodiment of the test card reading unit 54 of FIG. 3 is provided in FIG. 5. An important feature of this embodiment is the use of an "interpretation means", such as interpreter 72, which will "read" the test card 22, along with an encoder 76 that may be employed to generate (e.g. print) a result summary 82. The result summary 82 is contemplated to possibly include one or more printed bar code indicia. In a preferred embodiment of this embodiment of the invention, the result summary 82 may be provided (printed) using standard bar code symbologies (such as Code 39, Interleaved 2 of 5, PDF417, etc.). Accordingly the result summary 82 could be read using "off-the-shelf" scanning devices and decoders to provide scanner 54a and decoder 54b of FIG. 4. An advantage of the arrangement of FIG. 5, is that the assaying means 32 need not be configured to provide and generate a source of data that is in a "standard" bar code symbology. For instance, rather than configuring the machine readable assaying means 32 in standard bar code language format, a customized configuration can be employed (by using, for example, optical scan sheets, and the like). It is the function of the interpreter 72 and the encoder 76 to then decipher this customized indicia pattern and provide a standard bar code indicia. The standard bar code pattern may then be scanned by low cost and readily available devices and apparatus, such as bar code reader 55 (as shown in FIG. 5).

The aforementioned configurations of the machine readable assaying system of the present invention, in one contemplated field of use, may utilize these systems on-site at a place of employment. For example, in a company that hires skilled and professional employees (that may be assumed to be in great demand), may employ the present invention on-site at the point when the company is going to hire said prospective employees. In a preferred embodiment, a donor individual may be given a collection container (not shown) and provided a private environment where the donor excretes a specimen or volume of physiological fluid, urine in this case, into the collection container for analysis. The volume of urine, or a portion thereof, may then be brought into suitable contact with the test card 22 (for example, by placing a small amount of urine on the card, inserting the test card 22 into the urine, or the like). The quality control indication means 38 may then be checked, say via scanning and decoding, to verify the integrity of the results indicated by the assaying means 32. Assuming that the assay system is functioning properly, the adulteration detection means 36 may then be checked to determined whether the donor individual may have tampered with the specimen. If the adulteration detection means 36 indicates that the specimen is unadulterated, then the machine readable assaying means 32 may be scanned and read by the test card reading unit 54 (such as the scanner 54a and decoder 54b). The results of the assay as provided by the scanned source of data (patterns) may then stored in the memory unit 62B of the controller module 62, and or transmitted to a predetermined remote location, such as the centralized facility 58 of FIG. 3.

Upon the central facility 58 (or other suitable remote location) receiving the assay data/information, the names or identification codes of the donor individuals who provided negative results may be immediately communicated to the prospective employer, so that those particular donors may be offered employment. The urine sample providing a positive assay result may be requested from the on-site location (e.g., the company considering hiring the prospective employee), to be sent to the central facility 58 for further analysis and confirmation. Accordingly, an employer utilizing the present invention either directly and or indirectly via a third party is provided with a quick 'turn-around' time for receiving test results, and thereby may much more rapidly tender offers to qualified individuals that provided a negative assay. In addition, the privacy concerns of the donors are clearly safeguarded.

Figure 6:
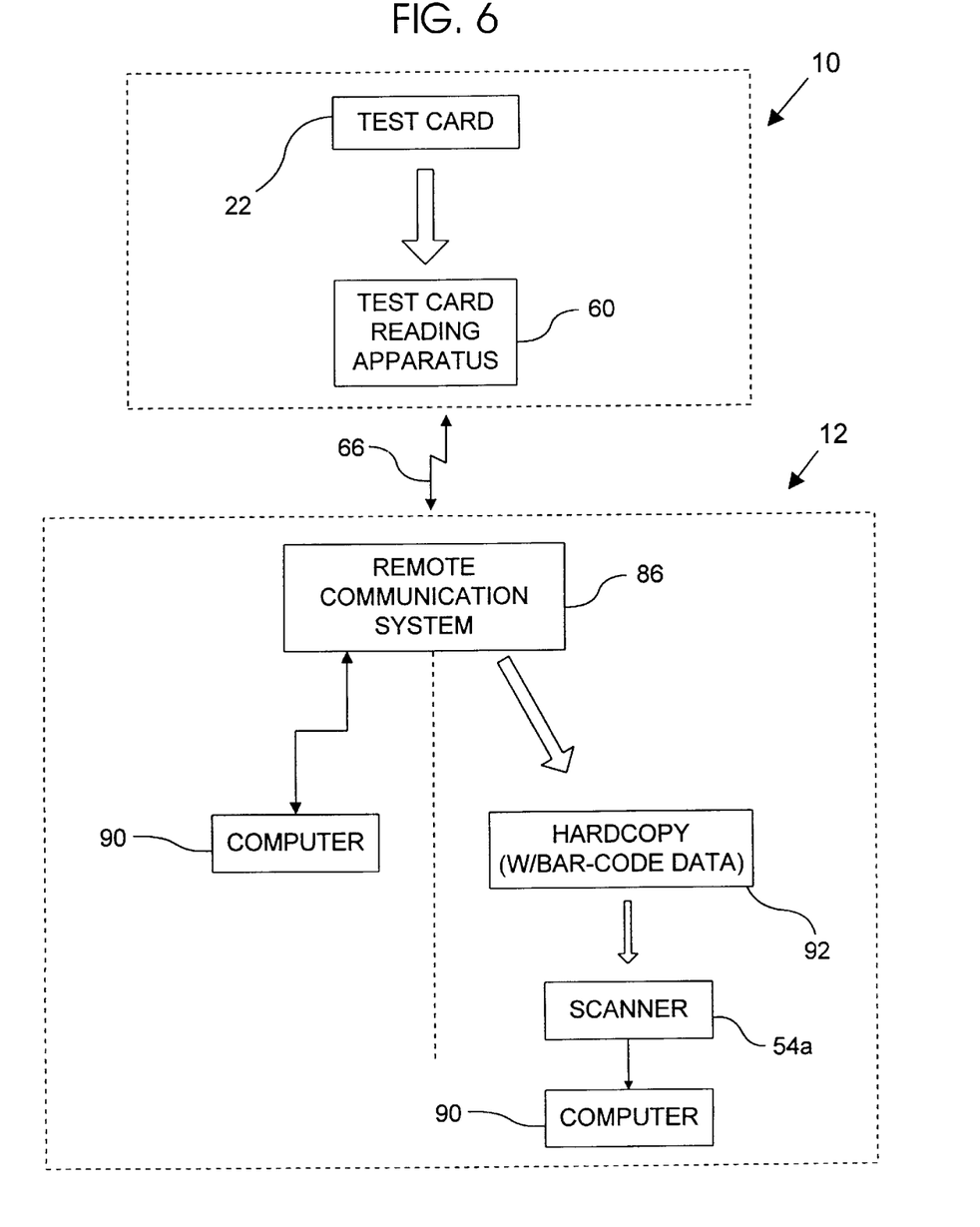
FIG. 6 is a high level functional diagram depicting embodiments of assaying arrangements in accordance with the present invention.

In order to further understand the present invention, and the possible embodiments thereof that may be provided, attention is called to FIG. 6. The assaying system, as illustrated in FIG. 6, is designated 10. The test card 22 and suitable test card reading apparatus 60 will be used, as addressed above, to assay a volume of physiological fluid (e.g., urine, saliva, sweat, or blood). Once the test card 22 is contacted with the fluid, and a sufficient temporal period has elapsed, the test card 22 may be scanned and read, with the various determined and decoded sources of data (upon the test card 22), say a plurality of characters or digits, or alternately as one or more scannable bar-code indicia, may be transmitted to the remote location, including a central data processing facility, a suitable laboratory, or other selected and appropriate location. At the remote location 12 a remote communication system 86 may be configure to communicate the received information directly to a computer 90 or produce a hard copy 92 (possibly including one or more bar-code indicia) that may be scanned or generally entered into computer 90. Regardless of the architecture of the remote communication system 86 and associated components, the transmitted data and information is coupled to the computer 90 for evaluation, decoding, and or analysis, in order to rapidly determine if a respective assay is negative. Once the result of an assay is determined, say, to be negative, the employer may be rapidly notified. Such notification may be almost immediate and supported by the remote communication system 86 and the assaying system 10.

It is must be understood that the architectural and operational embodiments described herein are exemplary of a plurality possible to provide the same (or equivalent) general system operation and features. Therefore, while there have been described the currently preferred embodiments of the present invention, those skilled in the art will recognize that other and further modifications may be made without departing from the present invention, and it is intended to claim all modifications and variations as fall within the scope of the described invention.

What is claimed is:

1. A machine readable assaying system for analyzing a volume of physiological fluid comprising:

a) a substrate; and b) analysis means located upon the substrate, the analysis means capable of detecting and optically providing a machine readable indication of the presence or absence of at least one specific substance that may be contained in the fluid, said analysis means including at least one analysis strip that upon contacting the physiological fluid of a donor individual for a suitable temporal interval changes from a first state having a first reflectance level to a second state having a second substantially different reflectance level, thereby providing an optically detectable change employable to alter the machine readable source of data to indicate at least one of the following: the presence of at least one specific substance or the absence of at least one specific substance;

c) at least one fixed strip and at least one blank region, which in conjunction with the analysis strips, form the alterable machine readable source of data.

2. The assaying system according to claim 1, further comprising:

a) means capable of optically scanning and reading the source of data provided by the assaying means upon the substrate after the analysis means has suitably contacted the volume of physiological fluid; and b) a communication module for establishing a communication link, the communication module capable of transmitting the read machine readable source of data to a remote location via the communication link.

3. The assaying system according to claim 1, wherein the machine readable source of data is provided by at least one bar-code symbol comprised, at least in part, by the analysis strips.

4. The assaying system according to claim 3, wherein the substrate further includes at least one of:

a) adulteration detection means capable of determining whether a the volume of physiological fluid may have been tampered with;

b) quality control indication means capable of determining if the analysis strips are functioning properly; and c) test card production information.

5. The assaying system according to claim 4, wherein the adulteration detection means, quality control indication means, and the test card production information may each be provided as machine readable sources of data.

6. An on-site machine readable assaying system for detecting the presence or absence of at least one proscribed substance in a volume of physiological fluid emanating from a donor, the assaying system comprising:

a) a test card; and b) machine readable assaying means having at least one individual analysis strip provided upon the test card, each analysis strip including reagents capable of detecting and optically signaling the presence of at least one substance within the physiological fluid, upon contacting said fluid for a suitable temporal interval;

c) the test card further having at least one fixed strip and at least one blank region arranged along with the analysis strips to form a machine readable pattern, wherein the analysis strips upon contacting the physiological fluid of the donor, may effect a change from a first state having a first reflectance level to a second state having a second substantially different reflectance level, and thereby possibly altering the initial machine readable pattern to provide a second distinguishable machine readable pattern;

d) a scanable machine readable bar-code symbol, formed by the pattern, comprised of bar and space elements, the elements provided by the fixed strips, blank regions, and analysis strips.

7. The assaying system according to claim 6, further including adulteration detection means capable, upon contacting the physiological fluid, of determining if the physiological fluid may have been tampered with.

8. The assaying system according to claim 7, wherein the test card further includes quality control indication means configured to determine, upon contact with the physiological fluid, if the analysis strips of the machine readable assaying means are functioning properly, regardless of the presence or absence of any proscribed substances.

9. The assaying system according to claim 8, wherein the adulteration detection means and quality control indication means are included within the machine readable pattern of the test card.

10. The assaying system according to claim 9, wherein the machine readable source of data includes test card production information.

* * * * *